United States Patent
Zaharchuk et al.

(10) Patent No.: US 10,997,716 B2
(45) Date of Patent: May 4, 2021

(54) CONTRAST DOSE REDUCTION FOR MEDICAL IMAGING USING DEEP LEARNING

(71) Applicant: The Board of Trustees of the Leland Stanford Junior University, Stanford, CA (US)

(72) Inventors: Greg Zaharchuk, Stanford, CA (US); Enhao Gong, Sunnyvale, CA (US); John M. Pauly, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 232 days.

(21) Appl. No.: 16/155,581

(22) Filed: Oct. 9, 2018

(65) Prior Publication Data
US 2019/0108634 A1    Apr. 11, 2019

Related U.S. Application Data

(60) Provisional application No. 62/750,068, filed on Oct. 9, 2017.

(51) Int. Cl.
*G06T 7/00* (2017.01)
*G06T 3/60* (2006.01)
(Continued)

(52) U.S. Cl.
CPC ............ *G06T 7/0012* (2013.01); *G06N 3/08* (2013.01); *G06T 3/60* (2013.01); *G06T 5/002* (2013.01); *G06T 7/50* (2017.01); *G16H 30/40* (2018.01); *G06T 2207/10072* (2013.01); *G06T 2207/10081* (2013.01); *G06T 2207/10088* (2013.01); *G06T 2207/10121* (2013.01); *G06T 2207/10132* (2013.01); *G06T 2207/20081* (2013.01);
(Continued)

(58) Field of Classification Search
None
See application file for complete search history.

(56) References Cited

U.S. PATENT DOCUMENTS 10,096,109 B1 * 10/2018 Zaharchuk .............. G06T 3/60
10,665,011 B1 *  5/2020 Sunkavalli ............. G06T 15/80
(Continued)

OTHER PUBLICATIONS

Zhu G, Jiang B, Tong L, Xie Y, Zaharchuk G and Wintermark M (2019) Applications of Deep Learning to Neuro-Imaging Techniques, Front. Neurol. 10:869.doi: 10.3389/fneur.2019.00869 (Year: 2019).*
Fan et al, General Backpropagation Algorithm for Training Second-order Neural Networks, Aug. 17, 2017, https://arxiv.org/abs/1708.06243 (Year: 2017).*
(Continued)

*Primary Examiner* — Andrae S Allison
(74) *Attorney, Agent, or Firm* — Lumen Patent Firm (57) ABSTRACT

A method for diagnostic imaging with reduced contrast agent dose uses a deep learning network (DLN) [114] that has been trained using zero-contrast [100] and low-contrast [102] images as input to the DLN and full-contrast images [104] as reference ground truth images. Prior to training, the images are pre-processed [106, 110, 118] to co-register and normalize them. The trained DLN [114] is then used to predict a synthesized full-dose contrast agent image [116] from acquired zero-dose and low-dose images.

8 Claims, 8 Drawing Sheets

(51) Int. Cl.
  *G06N 3/08* (2006.01)
  *G06T 5/00* (2006.01)
  *G16H 30/40* (2018.01)
  *G06T 7/50* (2017.01)
  *G16H 50/20* (2018.01)

(52) U.S. Cl.
  CPC ............... *G06T 2207/20084* (2013.01); *G06T 2207/20221* (2013.01); *G06T 2207/30004* (2013.01); *G16H 50/20* (2018.01)

(56) References Cited

U.S. PATENT DOCUMENTS

| | | | | |
|---|---|---|---|---|
| 2014/0270453 | A1* | 9/2014 | Guo | A61B 5/7225 382/131 |
| 2015/0025666 | A1* | 1/2015 | Olivieri | G06F 30/00 700/98 |
| 2015/0282719 | A1* | 10/2015 | Fielden | A61B 5/0263 600/419 |
| 2017/0339431 | A1* | 11/2017 | Zhang | G06T 3/4053 |
| 2019/0122348 | A1* | 4/2019 | Jensen | G06T 11/00 |
| 2019/0220977 | A1* | 7/2019 | Zhou | G06T 5/50 |

OTHER PUBLICATIONS

Sugimori, Classification of Computed Tomography Images in Different Slice Positions Using Deep Learning, Journal of Healthcare Engineering vol. 2018, Article ID 1753480, 9 pages, https://doi.org/10.1155/2018/1753480 (Year: 2018).*

Sumida1 et al, Deep convolutional neural network for reduction of contrast-enhanced region on CT images, Journal of Radiation Research, vol. 60, No. 5, 2019, pp. 586-594 doi: 10.1093/jrr/rrz030; Advance Access Publication: May 24, 2019 (Year: 2019).*

Chen et al, Low-dose CT via convolutional neural network, https://www.ncbi.nlm.nih.gov/pmc/articles/PMC5330597/; Published online Jan. 9, 2017. doi: 10.1364/BOE.8.000679 (Year: 2017).*

Martin-Gonzalez et al, Image fusion performed with noncontrast computed tomography scans during endovascular aneurysm repair, Published by Elsevier Inc. on behalf of the Society for Vascular Surgery. This is an open access article under the CC BY-NC-ND licens, 2015 (Year: 2015).*

S. U. Dar, M. Yurt, L. Karacan, A. Erdem, E. Erdem and T. Çukur, "Image Synthesis in Multi-Contrast MRI With Conditional Generative Adversarial Networks," in IEEE Transactions on Medical Imaging, vol. 38, No. 10, pp. 2375-2388, Oct. 2019, doi: 10.1109/TMI.2019.2901750. (Year: 2019).*

Junshen Xu et al., "200x Low-dose PET Reconstruction using Deep Learning," arxiv.org 1712.04119. Dec 12, 2017.

\* cited by examiner

CONTRAST DOSE REDUCTION FOR MEDICAL IMAGING USING DEEP LEARNING

CROSS-REFERENCE TO RELATED APPLICATIONS

This application claims priority from U.S. Provisional Patent Application 62/570,068 filed Oct. 9, 2017, which is incorporated herein by reference.

STATEMENT REGARDING FEDERALLY SPONSORED RESEARCH OR DEVELOPMENT

None.

FIELD OF THE INVENTION

This invention relates generally to medical diagnostic imaging. More specifically, it relates to imaging techniques that use contrast agents.

BACKGROUND OF THE INVENTION

Many types of medical imaging use contrast agents to enhance the visualization of normal and abnormal structures. Examples include conventional angiography, fluoroscopy, computed tomography (CT), ultrasound, and magnetic resonance imaging (MRI). It is often desirable to reduce the contrast agent dose in order to increase the safety of these agents. However, reduced dose reduces desired imaging enhancements, so this has not been possible.

For example, MRI is a powerful imaging technique providing unique information to distinguish different soft tissues and pathologies. Magnetic contrast agents with unique relaxation parameters are often administered to further boost the visibility of pathology and delineation of lesions. Gadolinium based contrast agents (GBCAs) are widely used in MRI exams because of their paramagnetic properties, for applications such as angiography, neuroimaging and liver imaging. However, although GBCAs are designed to avoid toxic release and have been widely applied in contrast enhanced MRI (CE-MRI) examinations to assist the diagnosis, there are several side effects resulting from GBCA administration. Therefore, there are many reasons why it would be advantageous to reduce the dosage of GBCA while preserving the enhanced contrast in MRI imaging. Similar problems are associated with administering contrast agents in other imaging modalities as well. Thus, it would be of benefit to be able to reduce the dose of contrast agents generally in diagnostic imaging techniques, without sacrificing the image enhancement benefits that the contrast agents provide.

BRIEF SUMMARY OF THE INVENTION

The present invention provides techniques to enhance image quality of diagnostic imaging modalities using a lower dose of contrast than is currently possible. This enables new opportunities for improving the value of medical imaging. In addition to MRI, the techniques are generally applicable to a variety of diagnostic imaging techniques including angiography, fluoroscopy, computed tomography (CT), and ultrasound.

Surprisingly, the techniques of the present invention are able to predict a synthesized full-dose contrast agent image from a low-dose contrast agent image and a pre-dose image.

The low dose may be any fraction of the full dose, but is preferably $1/10$ or less of the full dose. Significantly, naively amplifying the contrast enhancement of a $1/10$ low-dose CE-MRI by a factor of ten results in poor image quality with widespread noise and ambiguous structures. Even though the low-contrast image cannot be used for diagnosis directly, or by simply amplifying its uptake, the techniques of the present invention remarkably are able to recover the full contrast signal and generate predicted full-contrast images with high diagnostic quality. Specifically, in experimental tests, the method yielded significant improvements over the 10% low-dose images, with over 5 dB PSNR gains, 11% SSIM increased, and improvements in ratings on image quality and contrast enhancement.

Embodiments of the invention use a deep learning network, such as a Convolutional Neural Network for image-to-image regression, with a pre-contrast image and low-contrast image as input, and with a predicted full-contrast image as output. A residual learning approach is preferably used in prediction.

The method includes preprocessing to co-register and normalize between different images so they are directly comparable. This step is important since there are arbitrary different acquisition and scaling factor for each scan. Preferably, the average signal is used for normalization. The preprocessed images are then used to train the deep learning network to predict the full-contrast image from the pre-contrast and low-contrast images. The trained network is then used to synthesize full-contrast images from clinical scans of pre-contrast and low-contrast images. The techniques are generally applicable for any diagnostic imaging modality that uses a contrast agent. For example, imaging applications would include fluoroscopy, MRI, CT, and ultrasound.

In one aspect, the invention provides a method for training a diagnostic imaging device to perform medical diagnostic imaging with reduced contrast agent dose. The method includes a) performing diagnostic imaging of a set of subjects to produce a set of images comprising, for each subject of the set of subjects, i) a full-contrast image acquired with a full contrast agent dose administered to the subject, ii) a low-contrast image acquired with a low contrast agent dose administered to the subject, where the low contrast agent dose is less than the full contrast agent dose, and iii) a zero-contrast image acquired with no contrast agent dose administered to the subject; b) pre-processing the set of images to co-register and normalize the set of images to adjust for acquisition and scaling differences between different scans; and c) training a deep learning network (DLN) with the pre-processed set of images by applying zero-contrast images from the set of images and low-contrast images from the set of images as input to the DLN and using a cost function to compare the output of the DLN with full-contrast images from the set of images to train parameters of the DLN using backpropagation. The cost function may be, for example, an MAE loss function, or a mixture loss function with non-local structural similarities.

In another aspect, the invention provides a method for medical diagnostic imaging with reduced contrast agent dose. The method includes a) performing diagnostic imaging of a subject to produce a low-contrast image acquired with a low contrast agent dose administered to the subject, where the low contrast agent dose is less than a full contrast agent dose, and a zero-contrast image acquired with no contrast agent dose administered to the subject; b) pre-processing the low-contrast image and zero-contrast image to co-register and normalize the images to adjust for acquisition and scaling differences; and c) applying the low-contrast image and the zero-contrast image as input to a deep learning network (DLN) to generate as output of the DLN a synthesized full-dose contrast agent image of the subject; where the DLN has been trained by applying zero-contrast images and low-contrast images as input and full-contrast images as reference ground-truth images.

The low contrast agent dose is preferably less than 10% of a full contrast agent dose. The diagnostic imaging may be angiography, fluoroscopy, computed tomography (CT), ultrasound, or magnetic resonance imaging. For example, performing diagnostic imaging may include performing magnetic resonance imaging where the full contrast agent dose is at most 0.1 mmol/kg Gadolinium MRI contrast. In one embodiment, the DLN is an encoder-decoder convolutional neural network (CNN) including bypass concatenate connections and residual connections.

In another aspect, the invention provides a method for medical diagnostic imaging including a) performing diagnostic imaging of a subject to produce a first image acquired with a first image acquisition sequence and a second image acquired with a second image acquisition sequence distinct from the first image acquisition sequence, where zero contrast agent dose is administered during the diagnostic imaging; b) pre-processing the first image and the second image to co-register and normalize the images to adjust for acquisition and scaling differences; c) applying the first image and the second image as input to a deep learning network (DLN) to generate as output of the DLN a synthesized full-dose contrast agent image of the subject; wherein the DLN has been trained by applying zero-contrast images with different imaging sequences as input and full-contrast images acquired with a full contrast agent dose as reference ground-truth images.

DETAILED DESCRIPTION OF THE INVENTION

Embodiments of the present invention provide a deep learning based diagnostic imaging technique to significantly reduce contrast agent dose levels while maintaining diagnostic quality for clinical images.

Figure 1:
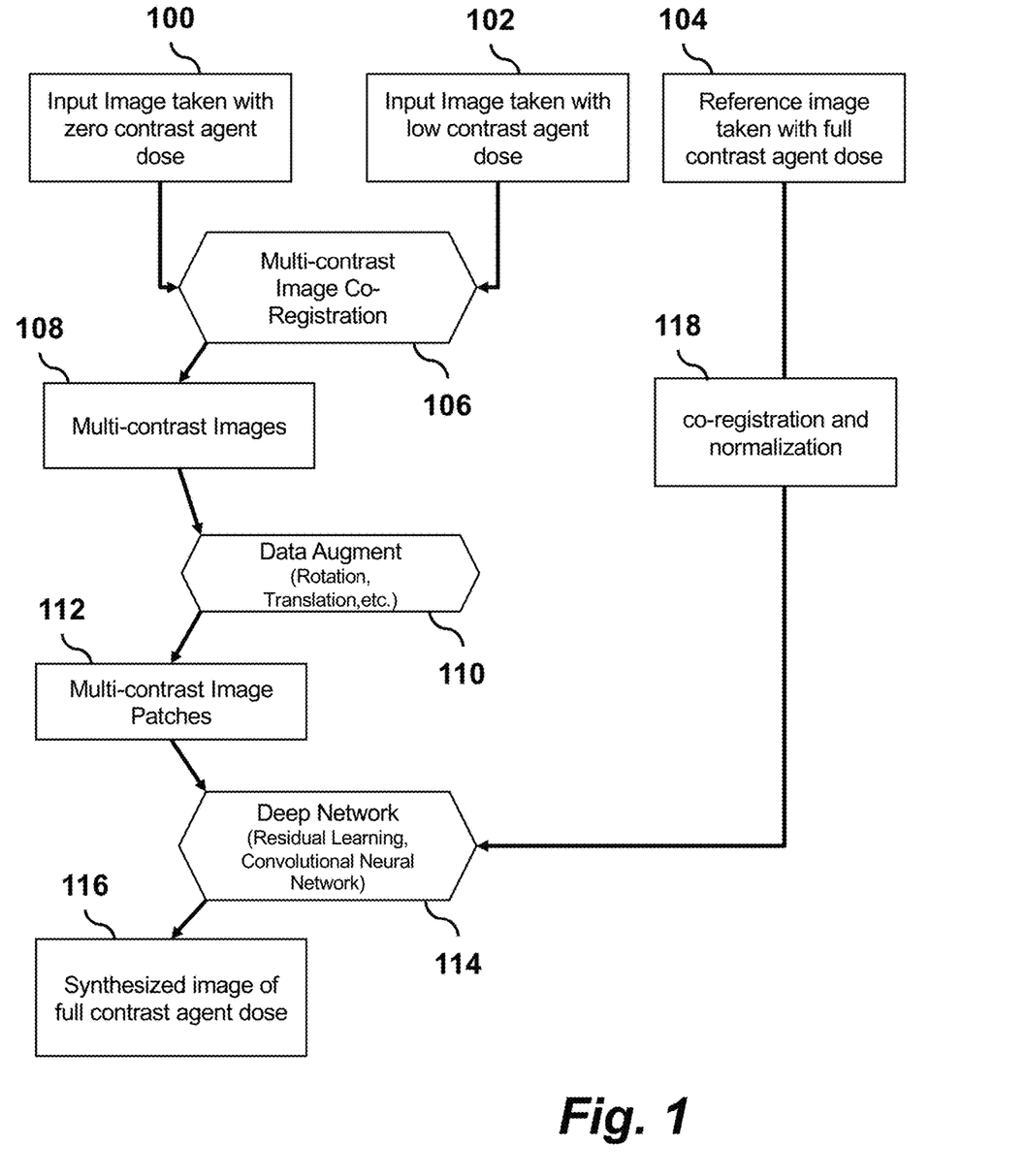
FIG. 1 is a flow chart showing a processing pipeline according to an embodiment of the invention.
Figure 2:
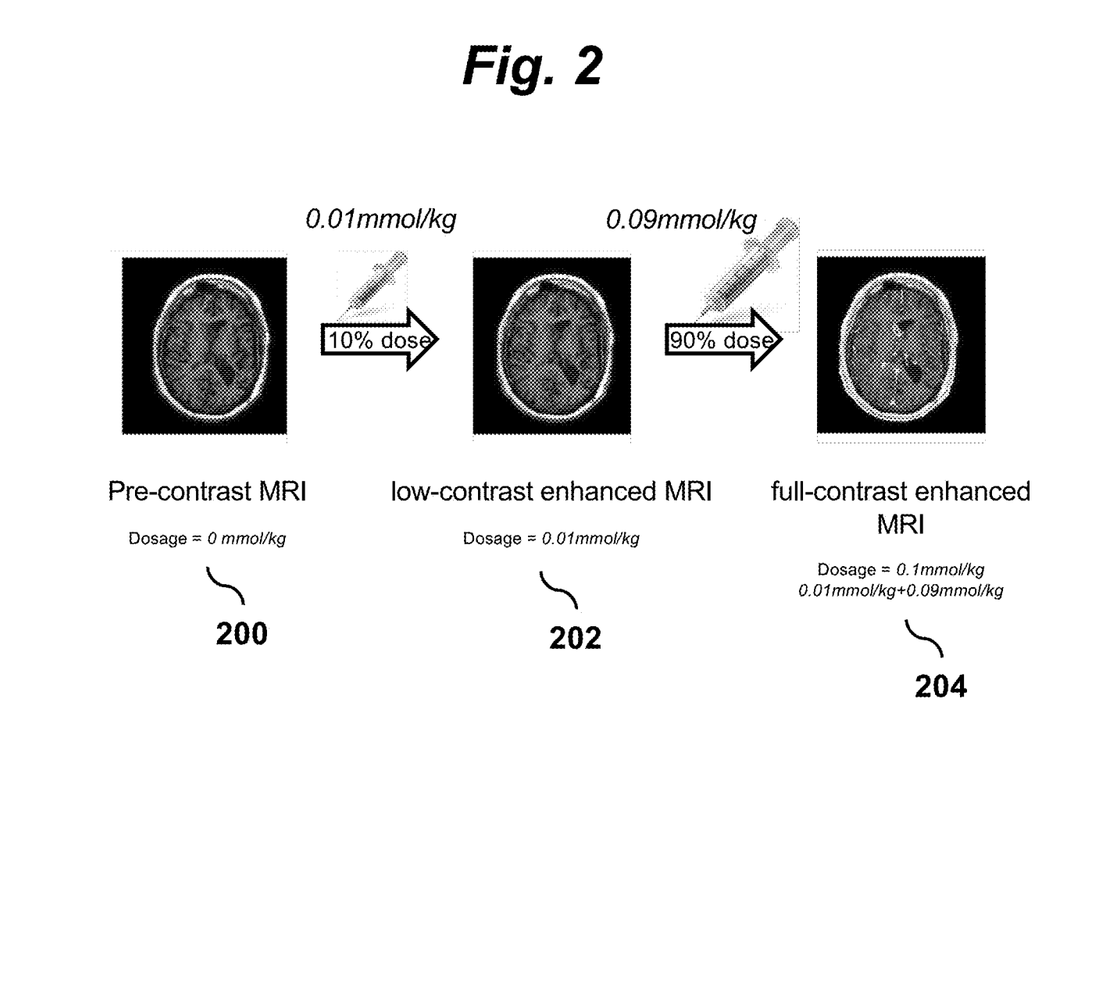
FIG. 2 illustrates a workflow of a protocol and procedure for acquisition of images used for training according to an embodiment of the invention.

Detailed illustrations of the protocol and procedure of an embodiment of the invention are shown in FIG. 1 and FIG. 2. Although the embodiments described below focus on MRI imaging for purposes of illustration, the principles and techniques of the invention described herein are not limited to MRI but are generally applicable to various imaging modalities that make use of contrast agents.

FIG. 1 is a flow chart showing a processing pipeline for an embodiment of the invention. A deep learning network is trained using multi-contrast images 100, 102, 104 acquired from scans of a multitude of subjects with a wide range of clinical indications. The images are pre-processed to perform image co-registration 106, to produce multi-contrast images 108, and data augmentation 110 to produce normalized multi-contrast image patches 112. Rigid or non-rigid co-registration may be used to adjust multiple image slices or volumes to match the pixels and voxels to each other. Since there can be arbitrary scaling differences between different volumes, normalization is used to match the intensity of each image/volume. Brain and anatomy masks are used optionally to extract the important regions of interests in each image/volume. Reference images 104 are also processed to perform co-registration and normalization 118. These pre-processed images are then used to train a deep learning network 114, which is preferably implemented using residual learning in a convolutional neural network. The input to the deep learning network is a zero-contrast dose image 100 and low-contrast dose image 102, while the output of the network is a synthesized prediction of a full-contrast dose image 116. During training, a reference full contrast image 104 is compared with the synthesized image 116 using a loss function to train the network using error backpropagation.

FIG. 2 illustrates the workflow of the protocol and procedure for acquisition of images used for training. After a pre-contrast (zero-dose) image 200 is acquired, a low dose (e.g., 10%) of contrast is administered and a low-dose image 202 is acquired. An additional dose (e.g., 90%) of contrast is then administered to total a full 100% dose, and a full-dose image 204 is then acquired.

In an MIll embodiment, images are acquired with 3T MIll scanners (GE Healthcare, Waukesha, Wis., USA) using standard neuro clinical protocol with high-resolution 3D T1-weighted inversion-recovery prepped fast-spoiled-gradient-echo (IR-FSPGR) imaging at 3T. Specifically, high-resolution T1-weighted IR-FSPGR pre-contrast images, post-contrast images with 10% low-dose and 100% full-dose of gadobenate dimeglumine (0.01 and 0.1 mmol/kg, respectively) full-dose images are acquired.

For other imaging modalities, similar setups are used to include at least one set of images without enhancement that is acquired without injecting contrasts. And optionally at least one set of images with low-level enhancement that is acquired with injecting low dosage of contrasts. For CT, the contrast is usually an iodine-based contrast agent. The CT contrast agent is usually administered based on preference of physicians, regulatory standard and patient weight. The administration of a low dose means injecting less than standard protocols. For CT there can be multiple set of images with different contrast visualization (possibly the same dosage but different visual appearance) by using multiple energy radiation. For CT, the ground-truth is a set of images acquired with 100% full-dose of CT contrast. For ultrasound, the contrast agent can be, for example, microbubbles. Similarly, the scans may contain at least one image with certain dosage of contrast and optionally images with variable dosage or images with dosage shown differently as acquired with different probe frequency.

Figure 3:
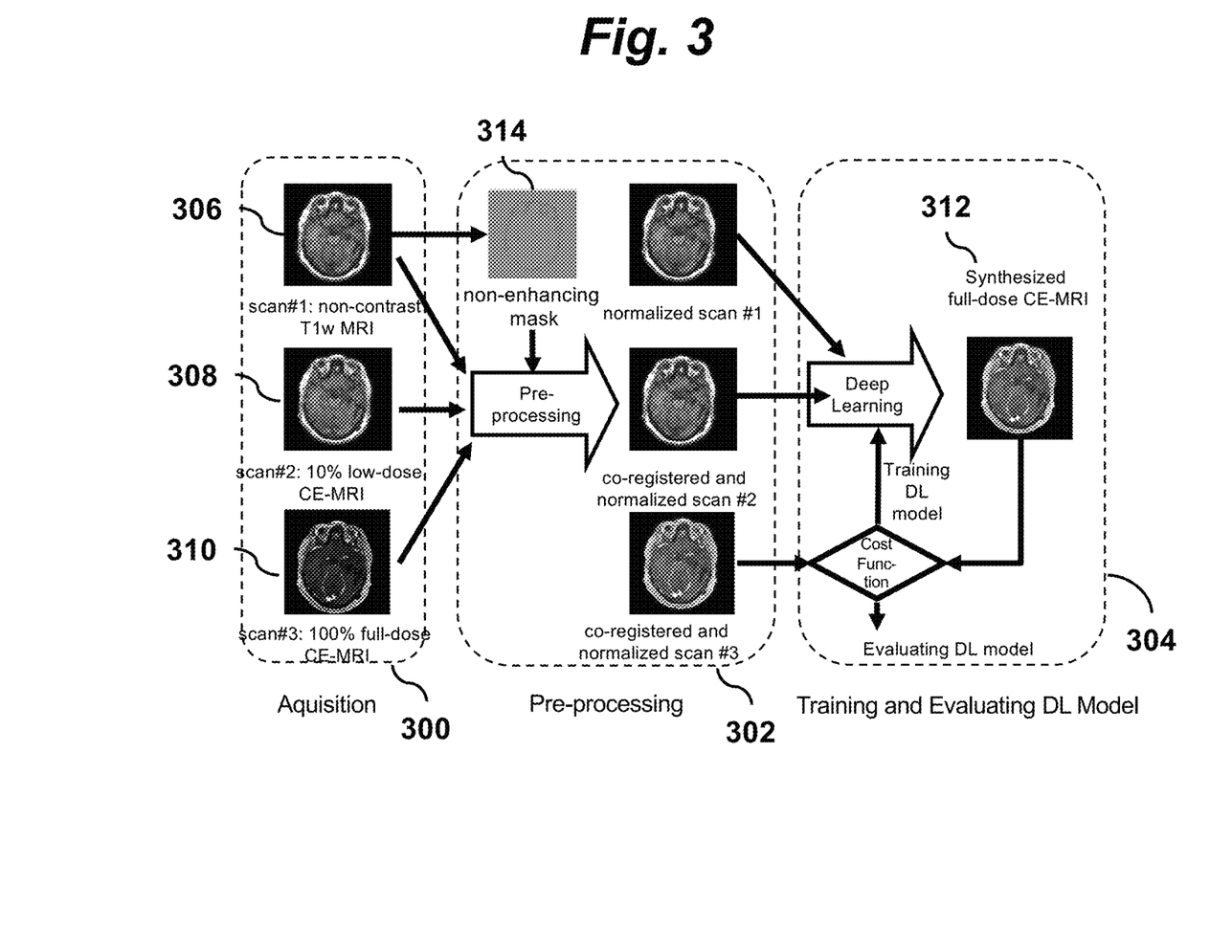
FIG. 3 is a schematic overview of an image processing flow according to an embodiment of the invention.

FIG. 3 is a schematic overview of the image processing flow. The steps of the detailed workflow are applied to the multi-contrast images acquired for each subject. In acquisition stage 300, scans are performed as described above to acquire a zero-contrast image 306, low-contrast image 308, and full-contrast image 310. These multi-contrast images then pass through a pre-processing stage 302. The resulting images then are used in a deep learning training stage 304 for training a deep learning network to synthesize a full-dose image 312. Pre-processing steps include image co-registration and signal normalization. Normalization is used to remove bias in the images obtained at different dosage levels, which is performed using a mask 314 of non-enhancing tissues. Specifically, to remove the systematic differences between different signal intensity levels in non-enhancing regions (such as scalp fat), co-registration and signal normalization based on average voxel value within a mask is performed. Alternatively, the normalization can be based on max/min intensity of the images or certain percentiles. Also, the normalization can be based on matching the distribution of intensity to certain predefined or standard distribution. Mask can be applied to calculate the average, max, min, percentile or the distribution to get better normalization performance to match different set of images. This step is performed because the transmit and receive gains used for 3 sequences of the 3 different scans are not guaranteed to be the same. For CT and ultrasound the scaling and normalization is also applicable as there are possible intensity re-scaling steps in both acquisition and image storage process.

Figure 4:
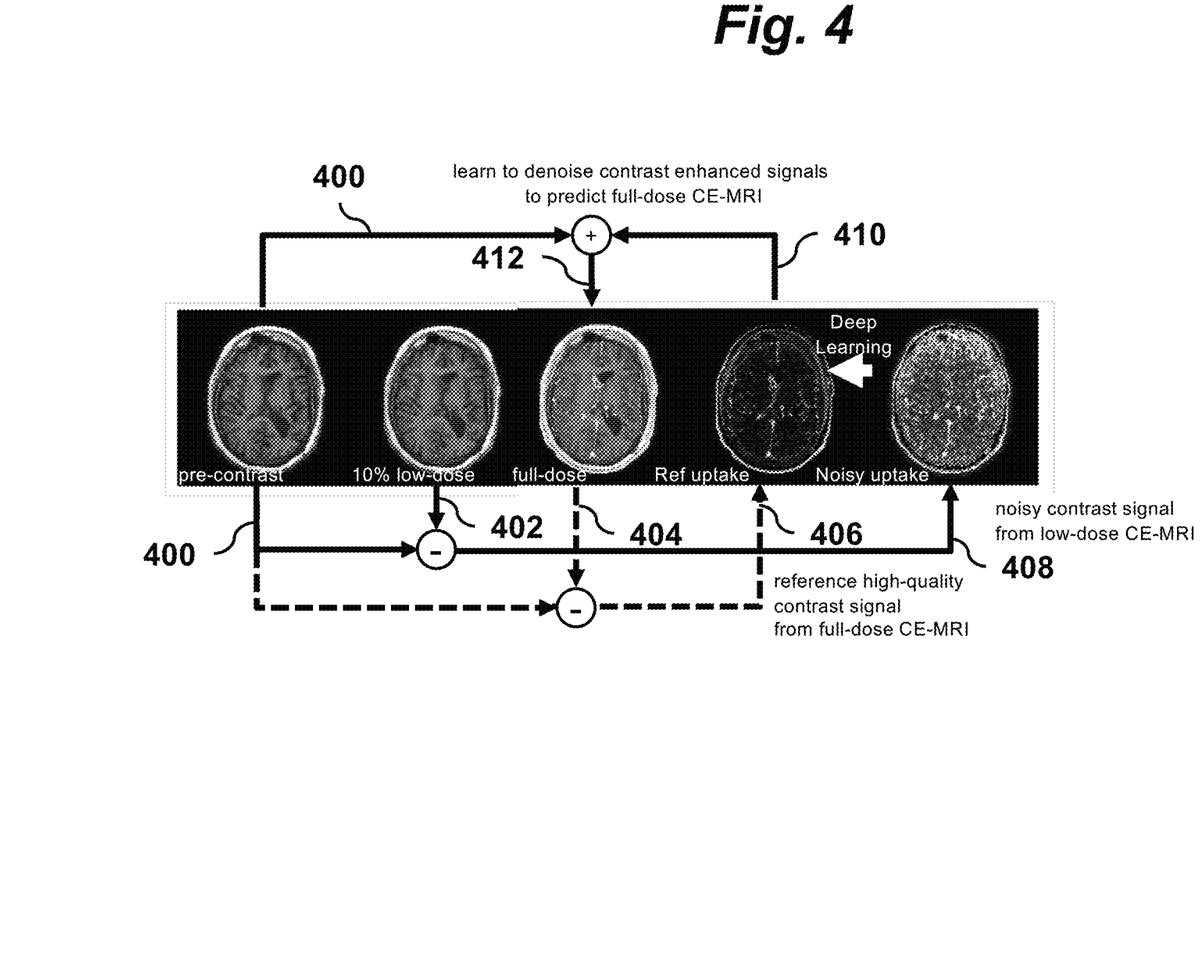
FIG. 4 is an illustration of a signal model to synthesize full-dose contrast-enhanced MRI image according to an embodiment of the invention.

After co-registration and normalization, the remaining signal differences between different contrast level images is in theory only related to contrast uptakes and non-structural image noise, as shown in FIG. 4, which is an illustration of the signal model to synthesize full-dose contrast-enhanced MM image 412. Compared with the reference high-quality contrast uptake 406 between pre-contrast 400 and full-dose 404 CE-MRI, the low-dose contrast uptake 408 between pre-contrast 400 and low-dose 402 is noisy but does include contrast information. By using a deep learning method, we learn the denoising to generate high-quality predicted contrast uptake 410 and then combine this with the pre-contrast scan 400 to synthesize a full-dose CE-MRI image 412.

After pre-processing, a deep learning network is trained using the true 100% full-dose CE-MRI images as the reference ground-truth. The non-contrast (zero-dose) MRI and the 10% low-dose CE-MRI are provided to the network as inputs, and the output of the network is an approximation of the full-dose CE-MRI. During training, this network implicitly learns the guided denoising of the noisy contrast uptake extracted from the difference signal between low-dose and non-contrast (zero-dose) images, which can be scaled to generate the contrast enhancement of a full-dose image.

Figure 5:
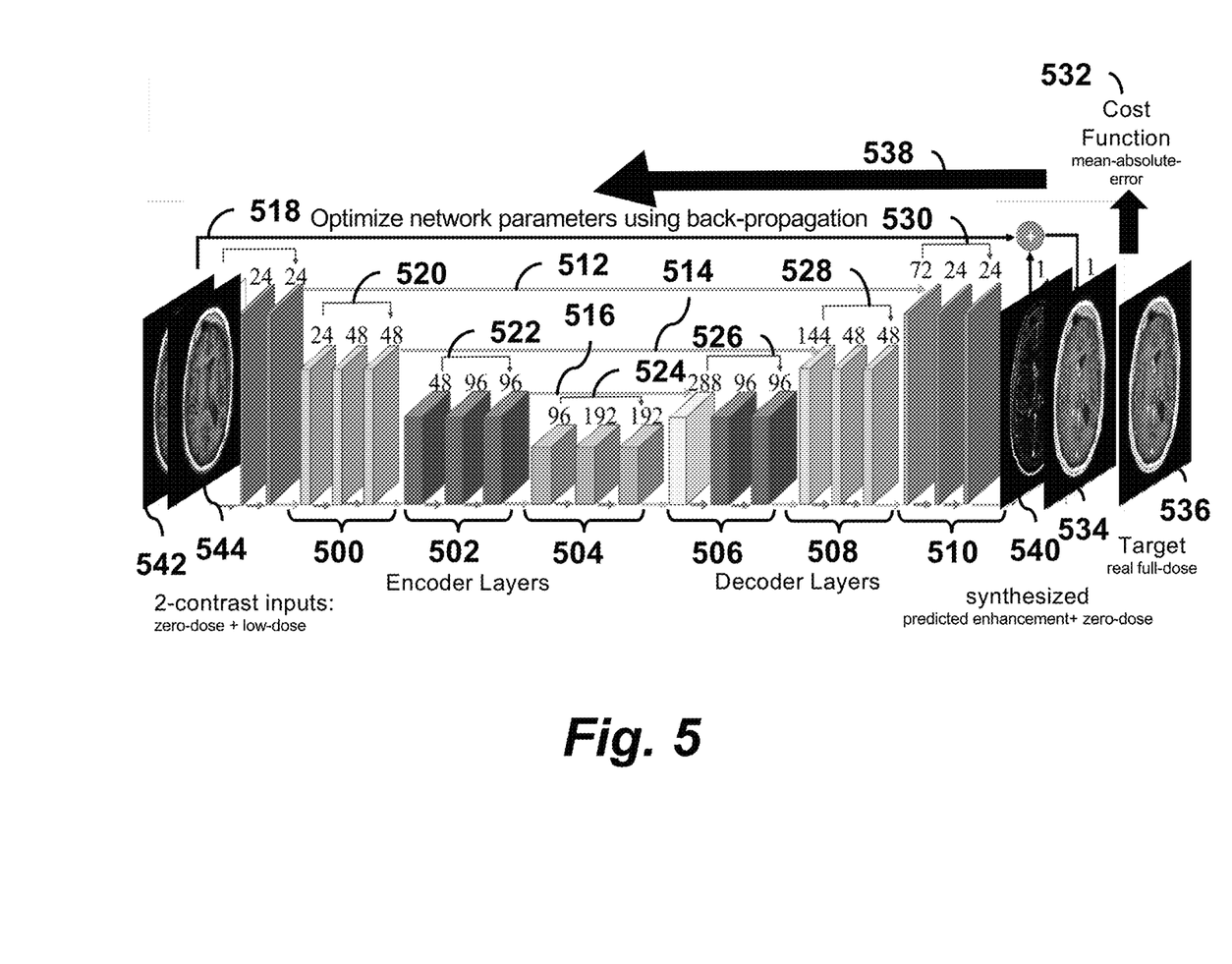
FIG. 5 shows a detailed deep learning (DL) model architecture according to an embodiment of the invention.

The detailed deep learning (DL) model architecture in one embodiment of the invention is shown in FIG. 5. This model is an encoder-decoder convolutional neural network with 3 encoder steps 500, 502, 504 and 3 decoder steps 506, 508, 510. In each step, there are 3 convolutional layers connected by 3×3 Conv-BN-ReLU. Encoding steps are connected in sequence by 2×2 max-pooling, and decoder steps are connected in sequence by 2×2 up-sampling. Bypass concatenate connections 512, 514, 516 combine symmetric layers to avoid resolution loss. The residual connections 518, 520, 522, 524, 526, 528, 530 enable the model to synthesize a full-dose image by predicting the enhancement signal 540 from a difference between pre-dose image 542 and low-dose image 544. The cost function 532 compares the predicted full-dose image 534 and the reference ground-truth full-dose image 536, which enables the optimization of the network parameters via error backpropagation 538.

The above-described network architecture is just one illustrative example. Other architectures are possible. For example, the network can have different number of layers, image size in each layers and variable connections between layers. The function in each layer can be different linear or nonlinear functions. The output layer can have a different so-called activation function that maps to certain range of output intensity. There can be multiple number of networks concatenated, so called recurrent network, that further improves the capability that one single network can achieve.

In one test, the network was trained on around 300 2D slices of the co-registered 3D volumes in each patient, excluding the slices at the base of the brain which had low SNR and no valuable information for anatomy or contrast. Standard image rigid transformations are used to further augment the dataset in training to ensure the robustness of the model.

In training, stochastic gradient descent (SGD) was used for each subset of training datasets and backpropagation is used to optimize the network parameters with respect to a cost function comparing predicted and true full-dose MR images. In one embodiment, the mean-absolute-error (MAE) cost function, also known as the L1 loss, is used in training. Training takes 200 epochs with SGD and ADAM method for optimization and 10% of the training dataset with random permutations was used for validation to optimize hyper-parameters and pick out the best model among all iterations. SGD and ADAM are also examples of operators to solve the optimization problem in training the network. There are many other options including, for example, RMSprop and Adagrad. Basically, the optimizers enable faster and smoother convergence.

The loss functions can include, for example, a function map from the ground-truth image and predicted image pair to a set loss values. This includes pixel-wise or voxel-wise loss that is based on pixel/voxel differences which usually use L1 (mean-absolute-error) or L2 (mean-squared-error) loss. Also, the loss can be based on regions with certain size that considering similarity of the structures, e.g., SSIM structural similarities. Or the loss can be computed based on other previously or concurrently trained networks that so-called perceptual loss or adversarial loss respectively. Also the loss can be any arbitrary weighted combination of many loss functions.

In a clinical setting, the trained deep learning network is used to synthesize a full-dose image from zero-dose and low-dose images. The co-registered and normalized non-contrast (zero-dose) and low-dose images are loaded from DICOM files and input to the trained network. With efficient forward-passing, which takes around 0.1 sec per 512-by-512 image, the synthesized full-dose image is generated. The process is then conducted for each 2D slice to generate entire 3D volume and stored in a new DICOM folder for further evaluation. For both training and testing the neural network, we used the Keras framework with Tensorflow backend, CUDA8 and CUDNN5.1, on a Linux server with 2 NVIDIA GTX 1080-TI GPUs. This is but one illustrative example. There are many alternative software and hardware implementations of deep networks that may be used.

In tests of the technique, the synthesized full-dose CE-MRI images contain consistent contrast uptake and similar enhancement. Detailed comparisons for several representative cases are discussed below, demonstrating that the method can generate synthesized full-dose contrast-enhanced MM with consistent enhancement but using lower dose (e.g., 1/10 full dose).

Figure 6:
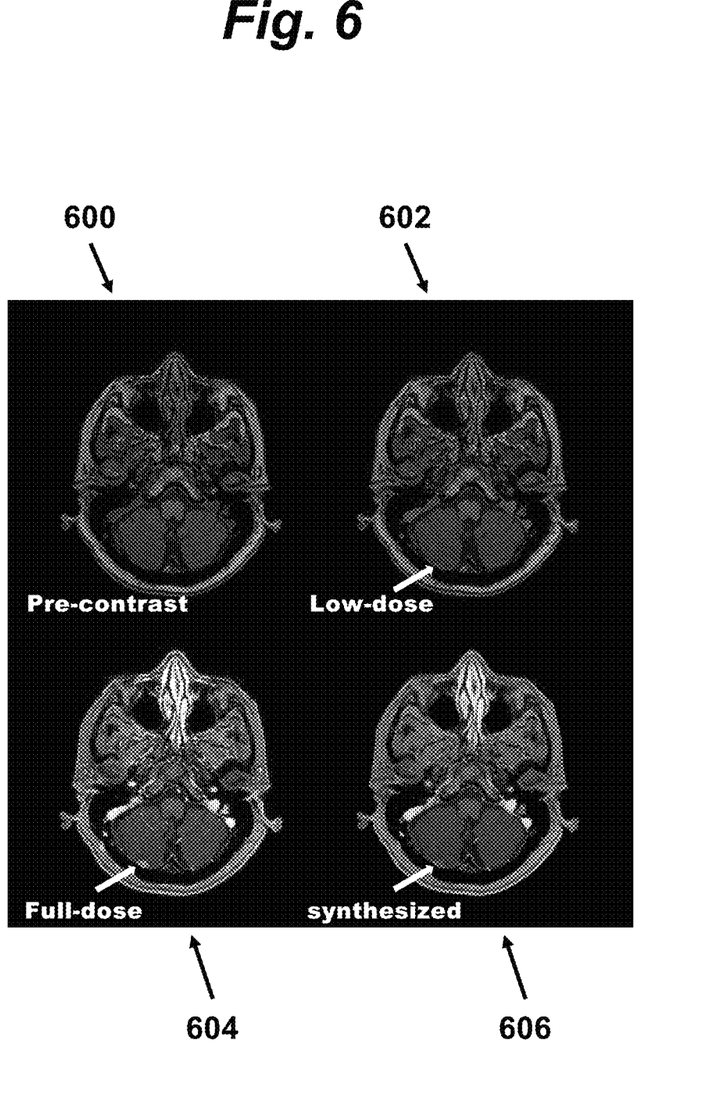
FIG. 6 is a set of images of a patient with intracranial metastatic disease, showing the predicted image synthesized from pre-contrast image and low-dose image, compared with a full-dose image according to an embodiment of the invention.

As shown in FIG. 6, in a patient with intracranial metastatic disease, the predicted image 606 synthesized from pre-contrast image 600 and low-dose image 602 has similar highlighting of contrast enhancement in the lesions as full-dose image 604. The lesions show improved visibility in the synthesized full-contrast image 606 while they cannot be reliably appreciated in low-dose CE-MRI image 602. Moreover, the synthesized CE-MRI image 606 shows a similar outline of a metastatic lesion in the right posterior cerebellum compared with the one in true full-contrast CE-MM image 604.

Figure 7:
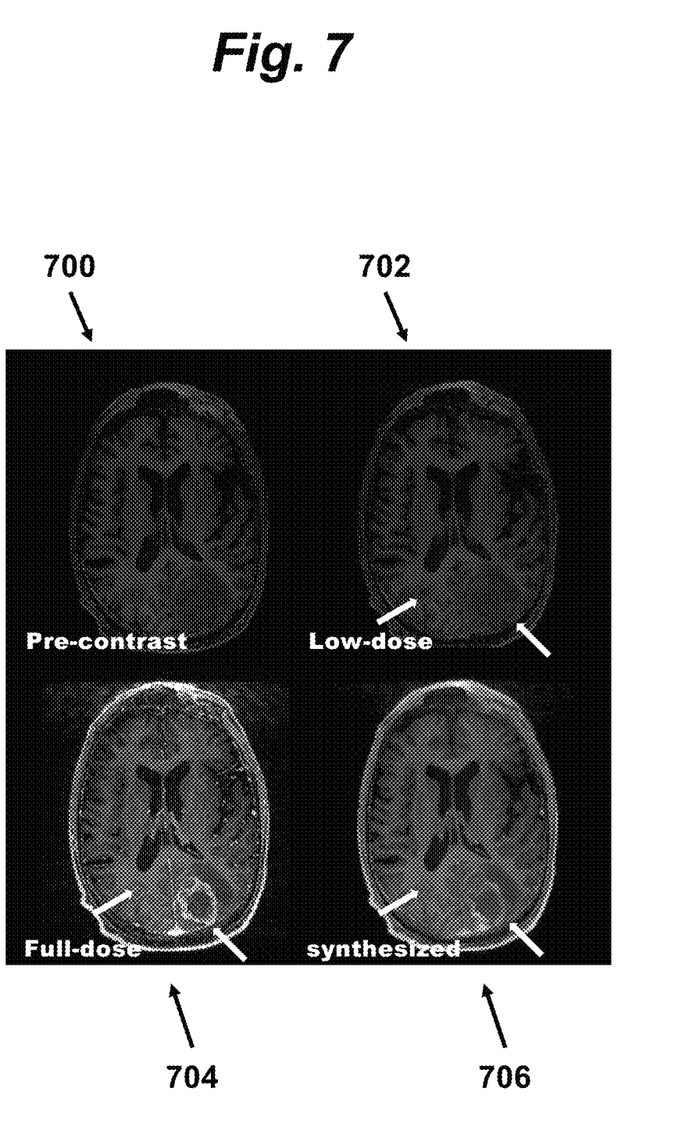
FIG. 7 is a set of images of a patient with a brain neoplasm, showing a synthesized full-dose image predicted from a pre-contrast image and low-dose image, compared with a full-dose image according to an embodiment of the invention.

For another case in a patient with a brain neoplasm, shown in FIG. 7, the synthesized full-dose CE-MM image 706 predicted from the pre-contrast image 700 and low-dose image 702 shows similar contrast uptake as in the real full-dose CE-MRI image 704. Plus, the image quality of the synthesized full-dose image 706 is better compared with the acquired full-dose CE-MRI 704 which has more severe motion artifacts and aliasing. Surprisingly, this demonstrates that the synthesized results have additional advantages over the original full-dose CE-MRI for better denoising and artifact removal, e.g., suppression of motion artifacts and aliasing.

Figure 8:
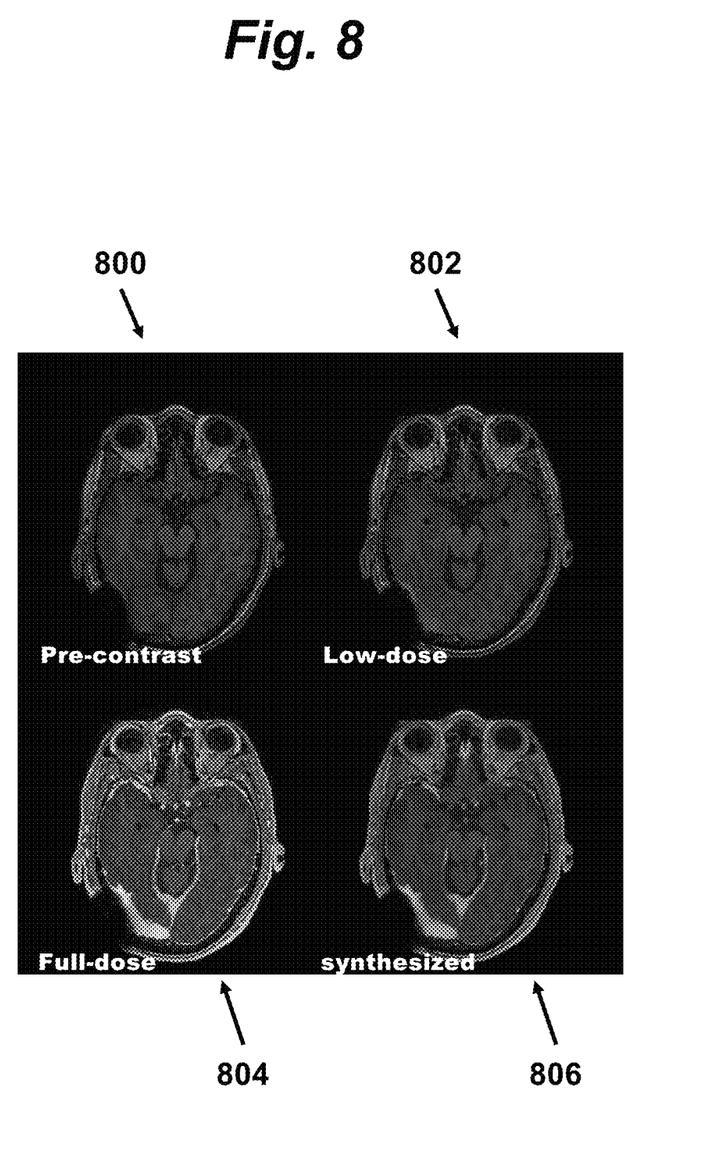
FIG. 8 is a set of images of a patient with a programmable shunt and intracranial hypotension, showing noise suppression capability and consistent contrast enhancement capability according to an embodiment of the invention.

In a case of a patient with a programmable shunt and intracranial hypotension, shown in FIG. 8, results also demonstrate better noise suppression capability and consistent contrast enhancement capability. The engorgement of the dural sinuses and pachymeningeal enhancement are clearly seen on both the synthesized image 806, predicted from pre-contrast image 800 and low-dose image 802, and true full-dose image 804, while there is less noise in non-enhancing regions on the synthesized image. Thus, the method generates diagnostic quality contrast from the low-dose acquisition, also demonstrating improved noise suppression and contrast enhancement.

Tests of the method by the inventors have demonstrated that the synthesized CE-MM images are improved significantly (both $p<0.001$) compared with the low-dose image on all quantitative metrics with 11.0% improvements in SSIM and over 5.0 dB gains in PSNR. Compared with the true acquired full-dose CE-MRI, the proposed method is not significantly different (both $p>0.05$) for overall image quality and the clarity of the enhanced contrast. Comparably, the 10% low-contrast images are significantly ($p<0.001$) worse in the clarity of the enhanced contrast, with a decrease of over 3 on a 5-point scale.

As FIG. 7 and FIG. 8 show, and as verified by neuroradiologists' ratings, the synthesized full-dose images show significant ($p<0.05$) improvements over the acquired full-dose CE-MRI in suppressing artifacts in the non-enhancing regions, which was an additional advantage of the DL method.

Compared with real full-dose CE-MRI, no significant differences ($p>0.05$) in contrast enhancements information could be identified by neuro-radiologists blinded to image origin. The synthesized full-dose images also appear to better suppress image artifacts ($p<0.05$). This is because the high-intensity signal of the real full-dose enhanced contrast inevitably augments motion/aliasing artifacts which are better suppressed when estimating contrast from the low-intensity contrast enhancements. The impact of being able to reduce contrast dose by 90% while retaining diagnostic information could have a large impact on patient well-being and imaging costs.

The illustrative embodiment described above uses a 2D CNN. Further performance gains are achievable with 3D CNN models considering the correlated spatial information in adjacent thin slices. Thus, the implementation of the invention illustrated with a 2D CNN is only an illustration, and 3D implementations are envisioned within the scope of the invention. More generally, 2D (process single slice of image), 2.5D (multiple slices of image), 3D (entire volume) and patch based (crop from volume) algorithms are envisioned.

In addition, the inventors envision that with more datasets, more complicated but powerful models such as generative models can be trained to further improve the contrast synthesis. Finally, although the MAE loss is used as cost function to train the DL model in the above illustrative embodiment, other loss functions are envisioned, such as mixture loss functions with non-local structural similarities or using Generative Adversarial Network (GAN) as a data driven cost function.

In the illustrative embodiment described above, a fixed level of gadolinium contrast is used with 90% reduction from the original clinical usage level.

More generally, the term full-dose is used herein to refer to a standard dosage enabling certain defined visual quality. Usually the contrasts are treated as drug and they have FDA regulated full-dose that should be used. The full-dose means a standard dosage that is recommended or required by the FDA or clinicians to achieve good diagnostic quality.

However, it is envisioned that additional reduction of the low dose is feasible by using alternative network structures and loss function, using larger training datasets with various pathologies as well as other complimentary information such as multi-contrast MRI, multiple imaging modalities, and patients' clinical history information. It is also envisioned that the technique can make use of a patch based method wherein the input image size can be different than 128×128×1. It can be any x×y×z size that uses a patch of size x×y and considering depth/thickness of z.

It is also envisioned that low dose levels higher than 10% may be used. In general, it is beneficial to minimize the dose subject to the constraint that the synthesized image retains diagnostic quality. The resulting minimal low dose may vary depending on contrast agent and imaging modality. It is also possible to base the training on more than two images having different dose levels, and it is not necessary to include a zero-dose image. In general, if the training dataset has a sufficient number of paired scans with two distinct dose levels, the network can be trained to automatically generalized to improve the lower dose $d_{low}$ to the higher dose $d_{high}$, where the higher dose level is a full dose or less, and the lower dose level is less than the high dose, i.e., $0 \leq d_{low} < d_{high} \leq 1$.

The inventors also envision synthesis of high dose images from zero dose images, without the need for any contrast dose images. The zero dose images in this case include multiple MR images acquired using different sequences (e.g., T1w, T2w, FLAIR, DWI) that show different appearance/intensity of different tissues. The trained network can then predict a synthesized full-contrast T1w to be used for diagnosis. Thus, according to this method, the deep learning network is trained with a first image acquired with a first image acquisition sequence and a second image acquired with a second image acquisition sequence distinct from the first image acquisition sequence, where zero contrast agent dose is administered during the diagnostic imaging when these images are acquired. In addition, images with other sequences may also be used. For example, in one embodiment, there are five images with five different sequences acquired. The training uses a reference ground truth T1w image acquired with full contrast agent dose. The images are pre-processed to co-register and normalize them to adjust for acquisition and scaling differences. The normalization may include normalizing the intensity within each contrast via histogram matching on median. Pre-processing may also include bias field correction to correct the bias field distortion via N4ITK algorithm. Pre-processing may also include using a trained classifier (VGG16) to filter out more abnormal slices. The deep learning network is preferably a 2.5D deep convolutional adversarial network. Using the trained network, a first image and second image acquired with different sequences are then used as input to the deep learning network (DLN) which then generates as output a synthesized full-dose contrast agent image of the subject.

The invention claimed is:

1. A method for training a diagnostic imaging device to perform medical diagnostic imaging with reduced contrast agent dose, the method comprising:
  a) performing diagnostic imaging of a set of subjects to produce a set of images comprising, for each subject of the set of subjects,
    i) a full-contrast agent dose image acquired with a full contrast agent dose administered to the subject,
    ii) a low-contrast agent dose image acquired with a low contrast agent dose administered to the subject, where the low contrast agent dose is less than the full contrast agent dose, and
    iii) a zero-contrast agent dose image acquired with zero contrast agent dose administered to the subject;
  b) pre-processing the set of images to co-register and normalize the set of images to adjust for acquisition and scaling differences between different scans;
  c) training a deep learning network (DLN) with the pre-processed set of images by
    applying zero-contrast agent dose images acquired with zero contrast agent dose from the set of images and low-contrast agent dose images acquired with low contrast agent dose from the set of images as input to the DLN and
    using a cost function to compare the output of the DLN with full-contrast agent dose images acquired with full contrast agent dose from the set of images to train parameters of the DLN using backpropagation.

2. The method of claim 1 wherein the cost function is an MAE loss function, or a mixture loss function with non-local structural similarities.

3. A method for medical diagnostic imaging with reduced contrast agent dose, the method comprising:
  a) performing diagnostic imaging of a subject to produce
    a low-contrast agent dose image acquired with a low contrast agent dose administered to the subject, where the low contrast agent dose is less than a full contrast agent dose, and
    a zero-contrast agent dose image acquired with zero contrast agent dose administered to the subject;
    wherein the low-contrast agent dose image and the zero-contrast agent dose image are acquired using a common imaging modality;
  b) pre-processing the low-contrast agent dose image and zero-contrast agent dose image to co-register and normalize the images to adjust for acquisition and scaling differences;
  c) applying the low-contrast agent dose image and the zero-contrast agent dose image as input to a deep learning network (DLN) to generate as output of the DLN a synthesized full-dose contrast agent image of the subject;
  wherein the DLN has been trained by applying zero-contrast agent dose images and low-contrast agent dose images as input and full-contrast agent dose images as reference ground-truth images.

4. The method of claim 3 wherein
the low contrast agent dose is less than 10% of a full contrast agent dose.

5. The method of claim 3 wherein
performing diagnostic imaging comprises performing angiography, fluoroscopy, computed tomography (CT), ultrasound, or magnetic resonance imaging.

6. The method of claim 3 wherein
performing diagnostic imaging comprises performing magnetic resonance imaging, and the full contrast agent dose is at most 0.1 mmol/kg Gadolinium MRI contrast.

7. The method of claim 3 wherein
the DLN is an encoder-decoder convolutional neural network (CNN) including bypass concatenate connections and residual connections.

8. A method for medical diagnostic imaging, the method comprising:
  a) performing diagnostic imaging of a subject to produce
    a first image acquired with a first image acquisition sequence and
    a second image acquired with a second image acquisition sequence distinct from the first image acquisition sequence,
    where zero contrast agent dose is administered during the diagnostic imaging;
    wherein the first image and the second image are acquired using a common imaging modality;
  b) pre-processing the first image and the second image to co-register and normalize the images to adjust for acquisition and scaling differences;
  c) applying the first image and the second image as input to a deep learning network (DLN) to generate as output of the DLN a synthesized full-dose contrast agent image of the subject;
  wherein the DLN has been trained by
    applying as input to the DLN zero-contrast agent dose images acquired with different imaging sequences and with a full contrast agent dose administered and
    using full-contrast agent dose images acquired with a full contrast agent dose administered as reference ground-truth images.

* * * * *

UNITED STATES PATENT AND TRADEMARK OFFICE
CERTIFICATE OF CORRECTION

PATENT NO. : 10,997,716 B2
APPLICATION NO. : 16/155581
DATED : May 4, 2021
INVENTOR(S) : Zaharchuk et al.

It is certified that error appears in the above-identified patent and that said Letters Patent is hereby corrected as shown below:

On the Title Page

Item (60), In the Related U.S. Application Data, the provisional application no. '62/750,068' should be changed to -- 62/570,068 --.

Signed and Sealed this
Nineteenth Day of April, 2022

Katherine Kelly Vidal
*Director of the United States Patent and Trademark Office*